United States Patent [19]

Schraga

[11] Patent Number: 5,628,764

[45] Date of Patent: May 13, 1997

[54] COLLAR LANCET DEVICE

[76] Inventor: Steven Schraga, 9433 Byron Ave., Surfside, Fla. 33181

[21] Appl. No.: 407,758

[22] Filed: Mar. 21, 1995

[51] Int. Cl.$^6$ ................................................ A61B 17/32
[52] U.S. Cl. ..................................... 606/182; 606/181
[58] Field of Search .............................. 606/182, 181, 606/167, 170, 183

[56] References Cited

U.S. PATENT DOCUMENTS

| | | | |
|---|---|---|---|
| 4,990,154 | 2/1991 | Brown et al. | 606/182 |
| 5,026,388 | 6/1991 | Ingalz | 606/182 |
| 5,318,584 | 6/1994 | Lange et al. | 606/182 |
| 5,350,392 | 9/1994 | Purcell et al. | 606/182 |

*Primary Examiner*—Guy V. Tucker
*Assistant Examiner*—Patrick W. Rasche
*Attorney, Agent, or Firm*—Malloy & Malloy, P.A.

[57] ABSTRACT

An improved collar lancet device having a lancet housing with an open first end and a plunger element contained within the housing such that a receiving end slides towards the open first end in such a manner as to be urged into a piercing orientation wherein the receiving end protrudes up to a maximum amount from the lancet housing upon triggered firing thereof. Further, the lancet device includes a disposable cap element including a lancet contained in a sheathed relation by a cap body structured for secure yet removable fitted engagement on the lancet housing, the lancet contained therein being structured for engagement within the receiving end of the plunger element such that when the plunger element moves to its piercing orientation a tip of a piercing member of the lancet protrudes from an aperture in the top end of the cap body before retracting to concealed orientation within the cap body. Further, the lancet and cap body are engaged with one another such that they cannot be removed from one another yet the lancet is able to slide relative to the cap body, and upon removal of the cap body from its fitted position atop the lancet housing the cap body will be locked into a sheathed orientation over the lancet, thereby preventing further repeated use of the used and possibly contaminated lancet contained therein.

20 Claims, 2 Drawing Sheets

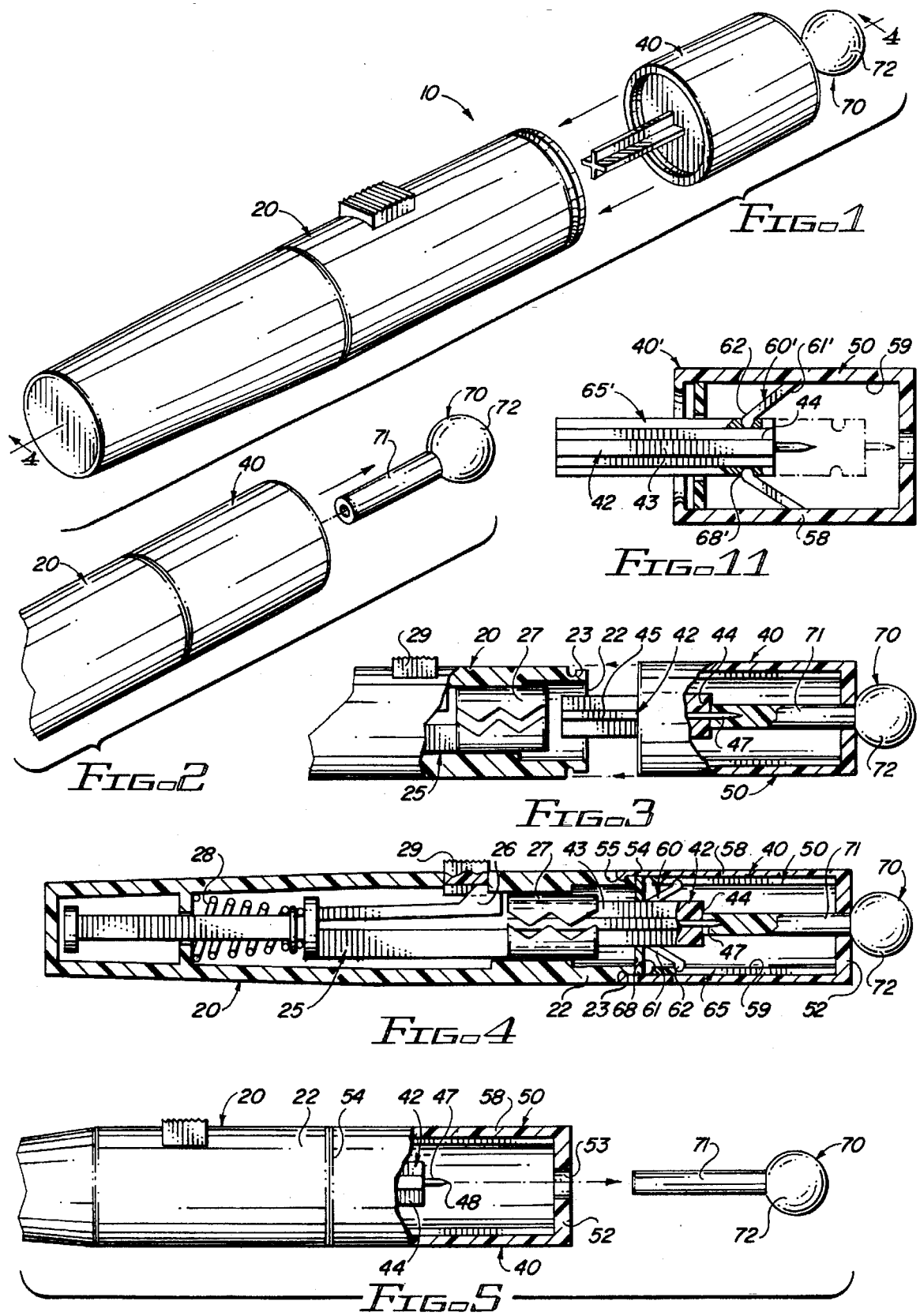

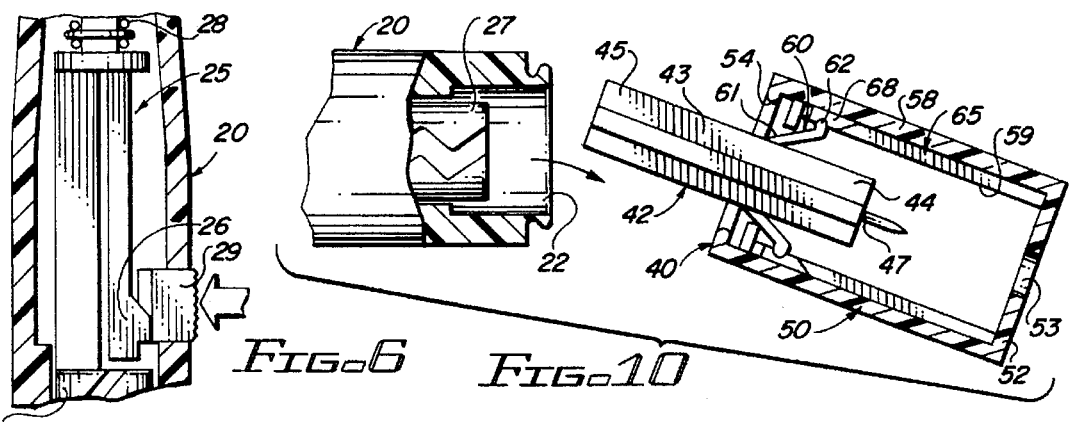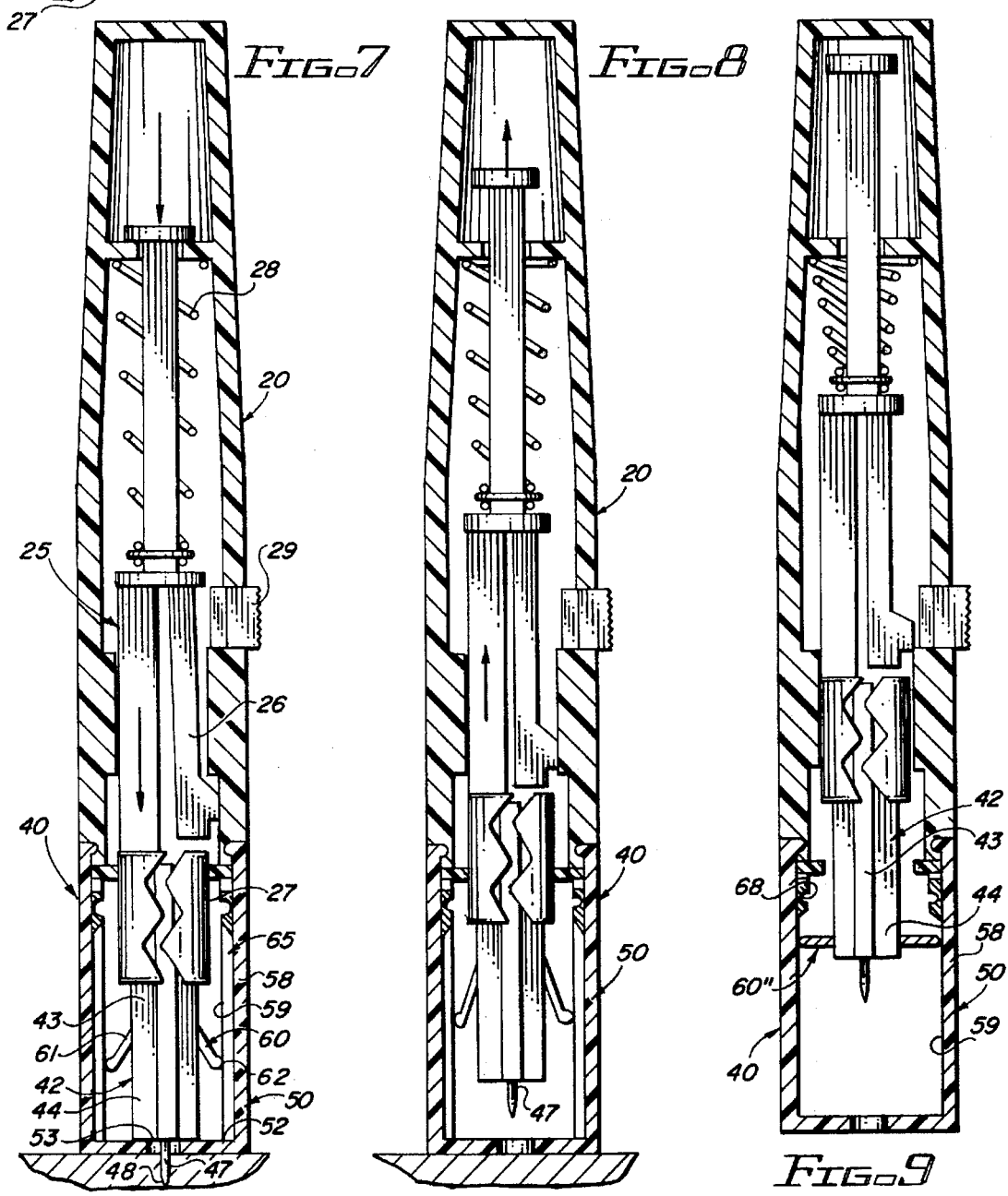

COLLAR LANCET DEVICE

BACKGROUND OF THE INVENTION

1. Field of the Invention

The present invention relates to an improved collar lancet device which not only functions effectively to pierce a patient's skin for blood sampling, but also provides for the substantially protected removal of the contaminated lancet piercing tip in such a manner as to prevent medical personnel or any other person using it from accidentally contacting a contaminated lancet tip during disposal thereof, and to further prevent the accidental reuse of a contaminated lancet tip.

2. Description of the Related Art

Lancet devices are frequently used instruments by both medical personnel and individuals in their own homes. Specifically, lancet devices are primarily adapted for facilitating the pricking of a finger or another portion of a patient, such as the ear lobe, to initiate a small amount of a blood sample for testing. As such, these devices are commonly used in hospitals and doctor's offices where blood tests are a frequent occurrence, as well as individually by some patients who must continuously administer medication such as insulin, to themselves and must repeatedly sample blood themselves.

A common and extremely dangerous hazard associated with the use of these types of lancet devices, especially given the advent of highly contagious and deadly, blood-transferred diseases such as the HIV Virus which causes AIDS or Acquired Immune-Deficiency Syndrome, relates to the ineffective and/or the inappropriate disposal of a contaminated lancet tip. Presently, most reusable lancet devices call for a small disposal tip portion to be inserted therein for subsequent firing to prick the patient's skin. Even these disposable tips however, while allowing a majority of the overall device to be re-used and disposal of only the contaminated portions, provide a significant hazard because they require the user to open the device and remove the used, contaminated tip from its secured position within the device. Simply put, accidents often still occur with these devices because the user generally attempts to recap the contaminated lancet tip and remove it from the device, and then dispose of it, both of which activities are hazardous. Specifically, although the lancet tip is sheathed for initial insertion into the lancet device, after use, a person must remove the used tip from the device, generally by gripping the lancet at or substantially near the contaminated pricking end. Next, if the user wishes to resheath the tip in the previously removed cover, precise and often substantially difficult maneuvering and placement must be implemented to ensure that the pricking end is not accidently mis-inserted or does not appropriately enter the sheathed cover, but rather pricks the finger of the person holding the sheathed cover. Such serious hazard associated with conventional disposal lancet tips, have thus lead to the production and development of single use lancet devices which are intended to be structured for allowing only a single prick of a finger, after which the entire device is disposed of, with the pricking tip maintained in a concealed location within the device. Such devices, however, can over time lead to a substantially increased expense, especially in hospital situations wherein a substantial number of blood samplings must be performed. Accordingly, there is a substantial need in the art for a device which will be substantially reusable, yet will provide for the safe and effective use and disposal of the lancet tip by removing the hazards associated with removal of a used tip from the reusable device.

The devices disclosed in the patents to Brown et al. (U.S. Pat. No. 4,990,154 and U.S. Pat. No. 5,074,872) have attempted to somewhat minimize the dangers involved with disposal of a contaminated lancet tip. As such, the lancet devices of Brown disclose a removable cap assembly which contains the lancet tip sheath therein. This device, while maintaining the lancet tip sheathed therein before and after use, does not eliminate the risk associated with accidental reuse. Specifically, the devices of Brown et al. incorporate a cap portion which holds the lancet tip therein in a retracted position. This device, when connected with the lancet body is structured such that during use a cocked hammer impacts a base of the lancet tip, momentarily urging it from the enclosed cap, and after firing, the tip is retracted back into the cap. At that point, however, the device of Brown et al. can easily be reused merely by recocking the hammer and firing it once again. Accordingly, if the lancet assembly of Brown is misplaced after use, a further user who does not know or recall that the assembly has already been contaminated can maneuver the assembly to cock the lancet once again for further firing of the hammer and for a dangerous re-use of a contaminated lancet tip. There is therefore a substantial need in the art for a lancet device which will not only completely conceal and contain a contaminated lancet tip after use and during disposal, but which will also eliminate the possibility that a contaminated lancet tip will be accidentally or intentionally reused. The device of the present invention is designed specifically to overcome these problems and does in fact function to ensure that a lancet tip is utilized only one time to prick the skin of a patient.

SUMMARY OF THE INVENTION

The present invention relates to an improved lancet device to be utilized effectively and efficiently in blood sampling procedures. A lancet device includes a lancet housing having a generally open first end containing a plunger element slidably disposed therein. The plunger element is structured with a receiving end that is positioned so as to protrude from the generally open end of the lancet housing. Further, the lancet device includes firing means which are structured and disposed to momentarily urge the plunger element into a piercing orientation wherein the receiving end of the plunger element protrudes a maximum amount through the generally open end of the lancet housing subsequent to initiation of triggering means.

Further, the lancet device of the present invention also includes a disposable cap element which is structured to be removably secured on the generally open end of the lancet housing. This disposable cap element includes therein a lancet having a generally elongate body with a distal end and a proximal end. Extending from the distal end of the elongate body is a piercing member which actually pierces the skin of the patient. Positioned in sheathed relation over the lancet is a cap body. The cap body includes a top end, a substantially open bottom end and a surrounding side wall structure, and as such defines an exterior portion of the disposable cap element. Further, the opened bottom end of the cap body is specifically structured for secure, yet removable fitted engagement on the generally open first end of the lancet housing such that when in position the cap body will substantially enclose the plunger element positioned within the lancet housing. Positioned at the top end of the cap is an aperture. This aperture is structured and disposed to permit passage of a tip of the piercing member of the lancet body therethrough. Particularly, in use the proximal end of the elongate body of the lancet is structured for secure, fitted engagement in the receiving end of the plunger element such that when the receiving end of the plunger element is momentarily urged into the piercing orientation, the tip of the piercing member of the lancet will extend momentarily through the aperture in the top end of the cap body prior to retracting to a concealed orientation within the cap body.

Also included as part of the disposable cap element, and disposed between the generally elongate body of the lancet end and an interior of the surrounding side wall structure of the cap body are engagement means. The engagement means are structured to maintain the lancet slidably secured to the cap body and will also include locking means. The locking means are structured so as to non-slidably secure the lancet in a sheathed orientation in the cap body upon pulled removal of the cap body from its secured, yet removably fitted engagement on the generally open end of the lancet housing, thereby ensuring that once the disposable cap element is pulled from the lancet housing, whether or not properly disposed of, it will not be reusable.

It is an object of the present invention to provide an improved lancet device which will prevent accidental and/or intentional reuse of a previously used lancet.

Another object of the present is to provide an improved lancet device which will be substantially reusable, thereby minimizing the costs associated therewith, while ensuring that the contaminated lancet portion thereof is appropriately and safely disposed of.

Yet another object of the present invention is to provide an improved lancet device which will provide for safe and easy removal of a contaminated lancet therefrom without jeopardizing the individual that must remove the used lancet from the device for appropriate disposal.

Also another object of the present invention is to provide a lancet device which does not require any added steps to appropriately cover or conceal a contaminated lancet after use, thereby ensuring that the contaminated lancet is appropriately covered and concealed for safe disposal.

Still another object of the present invention is to provide an improved lancet device which does not require any affirmative steps by a user, beyond merely removal of the contaminated portion from the housing in order to ensure that the contaminated tip will not be reused.

BRIEF DESCRIPTION OF THE DRAWINGS

For a fuller understanding of the nature of the present invention, reference should be had to the following detailed description taken in connection with the accompanying drawings in which:

FIG. 1 is a partially exploded perspective view of the lancet device of the present invention;

FIG. 2 is a partially exploded, isolated perspective view of the removal of the protective element of the lancet device of the present invention;

FIG. 3 is a cross-sectional view of a first embodiment of the lancet device illustrating initial securing of the lancet cap element to the housing;

FIG. 4 is a cross-sectional view of a first embodiment of the lancet device in a cocked, ready to fire orientation;

FIG. 5 is a cross-sectional view of a first embodiment of the lancet device in a cocked, ready to fire orientation illustrating removal of the protective element;

FIG. 6 is an isolated view of the preferred triggering means of the present invention;

FIG. 7 is a side cross-sectional view of the lancet device of the present invention in a firing orientation;

FIG. 8 is a side cross-sectional view of the lancet device of the present invention in a fired, retracted orientation;

FIG. 9 is a side cross-sectional view of another embodiment of the lancet device of the present invention;

FIG. 10 is an isolated, side cross-sectional view of the lancet device of the present invention upon removal of the disposable cap element;

FIG. 11 is a side cross-sectional view of another embodiment of the lancet device of the present invention;

Like reference numerals refer to like parts throughout the several views of the drawings.

DETAILED DESCRIPTION OF THE PREFERRED EMBODIMENT

Shown throughout the figures, the present invention is directed towards an improved collar lancet device, generally indicated as 10. The lancet device 10 is structured for reusable use in order to momentarily pierce the skin of a patient during blood sampling procedures. Specifically, the improved lancet device 10 of the present invention includes a lancet housing 20 with a generally open first end 22. This lancet housing 20, as with conventional lancet device housings, is preferably generally elongate so as to facilitate holding and handling by a user. Disposed within the lancet housing 20 is a plunger element 25. This plunger element 25 is slidably contained within the lancet housing such that it can move laterally therein, but preferably is structured such that it will protrude a certain maximum amount from the lancet housing 20 upon slided movement towards the open first end 22 of the lancet housing 20. In this regard, the plunger element 25 includes a receiving end 27 which moves towards and can protrude through the generally open first end of the lancet housing 20. Depending upon the specific dimensions of the lancet device 10, the receiving end 27 may not protrude at all from the open first end 22 of the lancet housing 20, however, preferably it will protrude at least a slight amount.

Also contained within the lancet housing 20, are firing means. The firing means are structured and disposed to rapidly and momentarily urge the plunger element 25 into a piercing orientation wherein a receiving end 27 of the plunger element 25 has moved a maximum amount towards and preferably through the generally open first end 22 of the lancet housing 20. As such, the firing means can take on any of a number of conventionally implemented configurations, but preferably will incorporate at least one spring 28 or other biasing means disposed within the lancet housing 20 and structured to rapidly move the plunger element 25 into the piercing orientation upon release of the plunger element 25 from a cocked orientation by triggering means. The triggering means, which can take on any of a number of conventionally implemented orientations, in the preferred embodiment will include an exteriorly protruding actuator button 29 which when pressed will release a retaining element 26 from its abutting, engaging contact with the lancet housing 20. This release of the retaining element 26 thereby releases the plunger element 25 for free movement towards the opened first end 22 of the lancet housing 20, as a result of the firing means. Further, as with conventional reusable lancet devices, unless the plunger element 25 is pushed substantially back into the lancet housing 20 after it has been fired. The plunger element 25 will not automatically and independently return to its cocked, ready to fire orientation.

Structured to be removably secured at the generally open first end 22 of the lancet housing 20 is a disposable cap element, generally indicated as 40. Included as part of the disposable cap element 40 is a lancet 42, surrounded by a cap body 50. Specifically, the lancet 42 includes a generally elongate body 43 with a distal end 44 and a proximal end 45. Further, disposed at the distal end of the generally elongate body 43 of the lancet 42 is a piercing member.

Turning to the cap body 50, it is positioned in sheathing relation over the lancet 42 and includes a top end 52, a substantially open bottom end 54 and a surrounding side wall structure 58 which defines the shape thereof. The open bottom end 54 of the cap body 50 is specifically structured for secure, yet removable fitted engagement on the generally open first end 22 of the lancet housing 20. Accordingly, when in place the cap body 50 will substantially enclose the plunger element 25 which protrudes through the generally open first end 22 of the lancet housing 20. In particular, the cap body 50 can be securely yet removably fitted to the lancet housing 20 in any of a variety of conventional configurations such as through the use of an interior rib 55 located at the open bottom end 54 of the cap body 50 which can snap-fit over a corresponding exterior rib 23 at the generally open first end 22 of the lancet housing 20. Nevertheless, any manner of engagement such as threaded engagement or mere frictional engagement can equivalently be incorporated, and the cap body 50 can be fitted on or in the lancet housing 20 directly or indirectly.

Included at the top end 52 of the cap body 50 is an aperture 53. This aperture 53 can be substantially small and is structured and disposed so as to permit passage of a tip 48 of the piercing member 47 which extends from the lancet 42 therethrough. In use, the proximal end 45 of the elongate body 43 of the lancet 42 is structured for secure, fitted engagement in the receiving end 27 of the plunger element 25. As such, the receiving end 27 of the plunger element 25 will hold the lancet 42 such that movement of the plunger element 25 will correspond movement of the lancet 42. In particular, when the receiving end 27 of the plunger element 25 is momentarily urged into its piercing orientation subsequent to firing, the tip 48 of the piercing member 47 of the lancet 42 will momentarily extend through the aperture 53 in the top end 52 of the cap body 50 so as to effectively prick a patient before retracting to a concealed orientation within the cap body 50 as the plunger element 25 returns to its at rest orientation in the lancet housing 20. Accordingly, in this configuration in order for the firing means of the device to move the plunger element 25 back into its piercing orientation, the plunger element 25 must be affirmatively pushed back into a cocked position, a procedure which necessarily requires removal of the cap body 50 from its orientation on the generally open first end 22 of the lancet housing 20 which substantially encloses the plunger element 25.

Disposed between the generally elongate body 43 of the lancet 42 and an interior 59 of the surrounding side wall structure 58 of the cap body 50 are engagement means. These engagement means are specifically structured to maintain the lancet 42 slidably secured to the cap body 50, thereby ensuring that the lancet 42 and cap body 50 do not separate from one another while permitting them to move relative to one another. Additionally included with the engagement means are locking means. These locking means are specifically structured and disposed to non-slidably secure the lancet in a sheathed orientation within the cap body 50 when the cap body 50 is removed from its secured fitted engagement on the generally open first end 22 of the lancet housing 20. In the preferred embodiment shown in FIGS. 1-8 and 10, the engagement means will include at least one, but preferably at least two protruding guide elements 60. In this preferred embodiment, the guide elements 60 each have a first end 61 and a second end 62, the fist end 61 being fixedly secured to the generally elongate body 43 of the lancet 42. Further, the second end 62 of the guide elements 60 will be slidably disposed in a corresponding guide track 65 disposed in the interior 59 of the surrounding side wall structure 58 of the cap body 50. As such, in use the guide elements 60 will ensure that appropriate slided orientation of the lancet 42 within the cap body 50 is maintained such that when the lancet 42 is moved momentarily to its piercing orientation, the tip 48 of the piercing 47 will appropriately and accurately protrude through the aperture 53 at the top end 52 of the cap body 50. Additionally, the second end 62 of the guide element 60 will be secured within the guide track 65 so as to prevent facilitated removal of the lancet 42 from its secure yet sliding engagement with the cap body 50. In particular, the lancet 42 can move laterally within the cap body 50, but will not be structured to be pulled from the opened bottom end 54 of the cap body 50 without actually breaking the disposable cap element 40 or the lancet 42. Although the preferred embodiment of the present invention includes the first end 61 of the guide element 60 fixedly secured to the lancet 42, with the second end 62 disposed in a guide track 65 on the interior 59 of the surrounding side wall structure 58 of the cap body 50, in an alternative embodiment, as in FIG. 11, the guide element 60' may be structured such that the first end 61' thereof is fixedly secured to the interior 59 of the surrounding side wall structure 58 of the cap body 50, while the second end 62' of the guide element 60' is slidably disposed in a corresponding guide track 65' disposed on the generally elongate body 43 of the lancet 42. Either orientation, however, of these preferred embodiments will equivalently result in the necessary slided movement between the lancet 42 and the cap body 50 while preventing removal of the lancet 42 from the cap body 50. Additionally, as in FIG. 9, the engagement means can include a guide collar that extends all or partially about the lancet 42, and can extend either from the cap body 50, as in the figure, or from the lancet 42. In this embodiment a guide track may or may not be included and the recess can extend completely around to engage the entire guide collar or can be in at least one, but preferably two or more locations there about.

Turning to the locking means of the engagement means, in the preferred embodiment, as illustrated in the figures, the locking means will include a recess 68 disposed in the guide track 65. In the first preferred embodiment, shown in FIGS. 1-8 and 10, the recess 68 will be disposed at a bottom end of the guide track 65. As such, when the lancet device 10 has been fired and disposal of the disposable cap element 40 is desired, a user looking to throw away the disposable cap element 40, and in fact a user wishing to mis-appropriately recock the plunger element 25 must grasp and remove the cap body 50 from its secure yet removal fitted engagement on the generally open first end 22 of the lancet housing 20. As the cap body 50 is removed, however, because the lancet 42 is allowed to freely slide therein, the lancet body 42 will remain, initially in its secure fitted engagement within the receiving end 27 of the plunger element 25. As such, this will cause the guide element 60 to slide downwardly along the guide track 65 until the second end 62 is securely and non-removably received within the recess 68. At this point, continued pulling of the cap body 50 will in turn pull the guide element 60 which can no longer move laterally within the guide track 65 due to its secure engagement within the recess 68, thereby pulling the lancet 42 from it secured engagement with the receiving end 27 of the plunger element 25. At that point, the overall disposable cap element 40 may be effectively discarded without fear of further use. As is evident from the previous description, this further use is prevented because even if the plunger element 25 is returned into a cocked orientation and the disposable cap element 40 is replaced thereon the lancet 42 will not be able to slide laterally relative to the cap body 50 into a piercing orientation. Similarly, in the second preferred embodiment, the recess 68' will be formed in a top end of the guide track 65' on the elongate body 43 of the lancet 42 such that as the cap body 50 is pulled from the lancet housing 20, the guide element 60' will slide up along the guide track 65' until the second end 62' falls within the recess 68' in order to pull the lancet 42 from the receiving end 27 of the plunger element 25.

Additionally, as an added safety as with most conventional disposable lancets, a protective element 70 having an elongate body 71 that extends through the aperture 53 in the top end 52 of the cap body 50 into initial covering relation over the piercing member 47 of the lancet 42. The protective element 70 has a protruding gripper knob 72 which is grasped for removal of the protected element 70 after initial engagement of the lancet 42 within the receiving end 27 of the plunger element 25 and positioning of the cap body 50 on the generally open first end 22 of the lancet housing 20.

Finally, as with some conventional types of lancet devices, the lancet housing or the disposable cap element can include depth adjustment means to vary an amount which the tip of the piercing end of the lancet protrudes through the aperture in the cap body. In the case of the disposable cap element, the adjustment means can be incorporated to space the engagement of the cap body with the lancet housing, or by varying the positioning of the top end of the cap body relative to the open bottom end of the cap body. Further, retracting means could be included within the cap body so as to assist or entirely cause retraction of the lancet into a sheathed position within the cap body. This retracting means can be a spring, an angled resilient flange or lip, or another, preferably biased, means that would tend to retract the lancet from a tip protruding orientation into a sheathed orientation, especially in circumstances wherein the receiving end of the plunger element does not securely hold the lancet so as to pull it back or is not structured to retract.

While this invention has been shown and described in what is considered to be a practical and preferred embodiment, it is recognized that departures may be made within the spirit and scope of this invention which should, therefore, not be limited except as set forth in the claims which follow and within the doctrine of equivalents.

Now that the invention has been described,
What is claimed is:
1. An improved collar lancet device comprising:
 (a) a lancet housing, said lancet housing including a generally open first end,
 (b) a plunger element slidably disposed in said lancet housing, said plunger element including a receiving end structured and disposed to move towards said generally open end of said lancet housing,
 (c) firing means structured and disposed to rapidly and momentarily urge said plunger element into a piercing orientation wherein said receiving end of said plunger element moves a maximum amount through said generally open end of said lancet housing,
 (d) triggering means structured and disposed to initiate the action of said firing means, and
 (e) a disposable cap element structured to be removably secured on said generally open end of said lancet housing, said disposable cap element comprising:
   a lancet, said lancet including a generally elongate body with a distal end and a proximal end,
   said lancet further including a piercing member extending from said distal end of said generally elongate body,
   a cap body disposed in sheathing relation over said lancet, said cap body including a top end, a substantially open bottom end and surrounding side wall structure,
   said open bottom end of said cap body being structured for secure, yet removable fitted engagement on said generally open first end of said lancet housing such that said cap body substantially encloses said plunger element,
   said top end of said cap body including an aperture disposed therein which is structured and disposed to permit passage of a tip of said piercing member of said lancet therethrough,
   said proximal end of said elongate body of said lancet being structured for secure, fitted engagement in said receiving end of said plunger element such that upon said receiving end of said plunger element being momentarily urged into said piercing orientation said tip of said piercing member of said lancet extends momentarily through said aperture in said top end of the said cap body before retracting to a concealed orientation within said cap body,
   engagement means disposed between said generally elongate body of said lancet and an interior of said surrounding side wall structure of said cap so as to maintain said lancet slidably secured to said cap body,
   said engagement means including at least one guide element having first fixedly secured end and a second slidable guide end, and
   lock means structured and disposed to immovably captivate said second slidable guide end of said guide element upon pulled removal of said cap body from said secure, yet removable fitted engagement on said generally open first end of said lancet housing, thereby preventing further slided movement of said lancet relative to said cap body and retaining said lancet in a sheathed orientation in said cap body.

2. An improved lancet device as recited in claim 1 wherein said disposable cap element further includes a protective element removably disposed in covering relation on said tip of said piercing end of said lancet and protruding through said aperture in said top end of said cap body so as to facilitate preliminary positioning of said proximal end of said elongate body of said lancet in said receiving end of said plunger element.

3. An improved lancet device as recited in claim 1 wherein said first end of said guide element is fixedly secured to said generally elongate body of said lancet and said second end of said guide element is slidably disposed in at least one guide track disposed in said interior of said surrounding side wall structure of said cap body.

4. An improved lancet device as recited in claim 3 wherein said locking means includes a recess disposed at a bottom end of said guide track in said interior of said surrounding side wall structure of said cap body, said recess being structured to securely and non-removably receive said second end of said guide element therein, upon pulled removal of said cap body from said secure, yet removable fitted engagement on said generally open first end of said lancet housing, thereby preventing movement of said lancet towards said top end of said cap body.

5. An improved lancet device as recited in claim 4 including at least two of said guide elements extending from opposite sides of said generally elongate body of said lancet into a corresponding one of at least two of said guide tracks disposed on opposite sides of said interior of said surrounding side wall structure of said cap body.

6. An improved lancet device as recited in claim 1 wherein said guide element includes a guide collar structured and disposed such that said first end of said guide element is fixedly secured to said generally elongate body of said lancet and said second end of said guide element is slidably disposed along said interior of said surrounding wall structured of said cap body.

7. An improved lancet device as recited in claim 1 wherein said first end of said guide element is fixedly secured to said interior of said surrounding wall structure of said cap body and said second end of said guide element is slidably disposed in at least one guide track disposed on an exterior of said generally elongate body of said lancet.

8. An improved lancet device as recited in claim 7 wherein said locking means includes a recess disposed at a bottom end of said guide track on said exterior of said generally elongate body of said lancet, said recess being structured to securely and non-removably receive said second end of said guide element therein, upon pulled removal of said cap body from said secure, yet removable fitted engagement on said generally open first end of said lancet housing, thereby preventing movement of said lancet towards said top end of said cap body.

9. An improved lancet device as recited in claim 8 including at least two of said guide elements extending from opposite sides of said interior of said surrounding side wall structure of said cap body into a corresponding one of at least two of said guide tracks disposed on opposite sides of said generally elongate body of said lancet.

10. An improved lancet device as recited in claim 1 wherein said guide element includes a guide collar structured and disposed such that said first end of said guide element is fixedly secured to said interior of said surrounding wall structure of said cap body and said second end of said guide element is slidably disposed along an exterior of said generally elongate body of said lancet.

11. A disposable lancet cap element to be used with a lancet device having a lancet housing, said lancet housing including a generally open first end, a plunger element slidably disposed in said lancet housing, said plunger element including a receiving end structured and disposed to move towards said generally open end of said lancet housing, firing means structured and disposed to rapidly urge said plunger element into a piercing orientation wherein said receiving end of said plunger element moves a maximum amount through said generally open end of said lancet housing, and triggering means structured and disposed to initiate the action of said firing means, said disposable lancet cap element comprising:

a lancet, said lancet including a generally elongate body with a distal end and a proximal end, said lancet further including a piercing member extending from said distal end of said generally elongate body, a cap body disposed in sheathing relation over said lancet, said cap body including a top end, a substantially open bottom end, and a surrounding side wall structure, said open bottom end of said cap body being structured for secure, yet removable fitted engagement on said generally open first end of said lancet housing such that said cap body substantially encloses said plunger element, said top end of said cap body including an aperture disposed therein which is structured and disposed to permit passage of a tip of said piercing member of said lancet therethrough, said proximal end of said elongate body of said lancet being structured for engagement with said receiving end of said plunger element such that upon said receiving end of said plunger element being urged into said piercing orientation said tip of said piercing member of said lancet extends through said aperture in said top end of said cap body, engagement means disposed between said generally elongate body of said lancet and an interior said surrounding side wall structure of said cap body so as to maintain said lancet slidably secured to said cap body, said engagement means including at least one guide element having a first fixedly secured end and a second slidable guide end, and locking means structured and disposed to immovably captivate said second slidable guide end of said guide element upon pulled removal of said cap body from said secure, yet removable fitted engagement on said generally open end of said lancet housing, thereby preventing further slided movement of said lancet relative to said cap body and retaining said lancet in a sheathed orientation in said cap body.

12. A disposable lancet cap element as recited in claim 11 wherein said first end of said guide element is fixedly secured to said generally elongate body of said lancet and said second end of said guide element is slidably disposed in at least one guide track disposed in said interior of said surrounding side wall structure of said cap body.

13. A disposable lancet cap element as recited in claim 12 wherein said locking means includes a recess disposed at a bottom end of said guide track in said interior of said surrounding side wall structure of said cap body, said recess being structured to securely and non-removably receive said second end of said guide element therein, upon pulled removal of said cap body from said secure, yet removable fitted engagement on said generally open first end of said lancet housing, thereby preventing movement of said lancet towards said top end of said cap body.

14. A disposable lancet cap element as recited in claim 13 including at least two of said guide elements extending from opposite sides of said generally elongate body of said lancet into a corresponding one of at least two of said guide tracks disposed on opposite sides of said interior of said surrounding side wall structure of said cap body.

15. A disposable lancet cap element as recited in claim 11 wherein said guide element includes a guide collar structured and disposed such that said first end of said guide element is fixedly secured to said generally elongate body of said lancet and said second end of said guide element is slidably disposed along said interior of said surrounding wall structured of said cap body.

16. A disposable lancet cap element as recited in claim 11 wherein said first end of said guide element is fixedly secured to said interior of said surrounding wall structure of said cap body and said second end of said guide element is slidably disposed in at least one guide track disposed on an exterior of said generally elongate body of said lancet.

17. A disposable lancet cap element as recited in claim 16 wherein said locking means includes a recess disposed at a bottom end of said guide track on said exterior of said generally elongate body of said lancet, said recess being structured to securely and non-removably receive said second end of said guide element therein, upon pulled removal of said cap body from said secure, yet removable fitted engagement on said generally open first end of said lancet housing, thereby preventing movement of said lancet towards said top end of said cap body.

18. A disposable lancet cap element as recited in claim 17 including at least two of said guide elements extending from opposite sides of said interior of said surrounding side wall structure of said cap body into a corresponding one of at least two of said guide tracks disposed on opposite sides of said generally elongate body of said lancet.

19. A disposable lancet cap element as recited in claim 11 wherein said guide element includes a guide collar structured and disposed such that said first end of said guide element is fixedly secured to said interior of said surrounding wall structure of said cap body and said second end of said guide element is slidably disposed along an exterior of said generally elongate body of said lancet.

20. A disposable lancet cap element as recited in claim 11 further including depth adjustment means structured and disposed to vary an amount which said tip of said piercing member of said lancet protrudes through said aperture in said top end of said cap body.

* * * * *